(12) United States Patent
Wirbisky et al.

(10) Patent No.: US 7,647,113 B2
(45) Date of Patent: Jan. 12, 2010

(54) ELECTRODE IMPLANTATION IN MALE EXTERNAL URINARY SPHINCTER

(75) Inventors: Alan G. Wirbisky, Brooklyn Park, MN (US); Andrew P. VanDeWeghe, St. Louis Park, MN (US)

(73) Assignee: AMS Research Corporation, Minnetonka, MN (US)

( * ) Notice: Subject to any disclaimer, the term of this patent is extended or adjusted under 35 U.S.C. 154(b) by 159 days.

(21) Appl. No.: 11/961,615

(22) Filed: Dec. 20, 2007

(65) Prior Publication Data

US 2008/0161876 A1 Jul. 3, 2008

Related U.S. Application Data

(60) Provisional application No. 60/871,188, filed on Dec. 21, 2006.

(51) Int. Cl.
*A61N 1/00* (2006.01)
(52) U.S. Cl. ...................................................... 607/41
(58) Field of Classification Search ............. 600/29–31, 600/373, 547, 553; 607/36, 37, 39, 40, 45, 607/61, 51, 66, 116, 118; 128/898
See application file for complete search history.

(56) References Cited

U.S. PATENT DOCUMENTS

| | | | |
|---|---|---|---|
| 3,628,538 A | 12/1971 | Vincent et al. | 128/422 |
| 3,662,758 A | 5/1972 | Glover | 128/419 |
| 3,870,051 A * | 3/1975 | Brindley | 607/40 |
| 4,044,774 A | 8/1977 | Corbin et al. | 128/404 |

(Continued)

FOREIGN PATENT DOCUMENTS

EP 1 119 314 10/1999

(Continued)

OTHER PUBLICATIONS

European Search Report and Written Opinion of 06011641.5 completed Aug. 21, 2006.

(Continued)

*Primary Examiner*—Angela D Sykes
*Assistant Examiner*—Robert N Wieland
(74) *Attorney, Agent, or Firm*—Jose' W. Jimenez; Kimberly K. Baxter; Gregory L. Koeller

(57) ABSTRACT

In a method of implanting an electrode of an electronic stimulator device into an external urinary sphincter of a male patient, a first incision is made in the perineum of the patient between the anus and the scrotal-perineal junction. A distal end of a stimulation lead is then fed through the first incision, through the perineal membrane and into the external urinary sphincter. The distal end includes the electrode. In one embodiment of the method, a second incision is made in the abdomen of the patient. In one embodiment, the second incision is made lateral to and cephalad to the pubis bone of the patient. Next, a proximal end of the stimulation lead is fed from the first incision to the second incision. In one embodiment, the proximal end of the stimulation lead is coupled to a control unit of the electronic stimulator device. Electrical signals are generated using the control unit and the electrical signals are delivered to the external urinary sphincter through the stimulation lead and the electrode.

25 Claims, 10 Drawing Sheets

U.S. PATENT DOCUMENTS

| | | | |
|---|---|---|---|
| 5,103,835 A | 4/1992 | Yamada et al. | 128/734 |
| 5,411,548 A | 5/1995 | Carman et al. | 607/138 |
| 5,520,606 A | 5/1996 | Schoolman et al. | 600/31 |
| 5,562,717 A | 10/1996 | Tippey et al. | 607/41 |
| 5,807,397 A | 9/1998 | Barreras et al. | 607/61 |
| 5,978,712 A | 11/1999 | Suda et al. | 607/41 |
| 6,061,596 A | 5/2000 | Richmond et al. | 607/41 |
| 6,328,686 B1 | 12/2001 | Kovac | 600/30 |
| 6,354,991 B1 | 3/2002 | Gross et al. | 600/29 |
| 6,862,480 B2 | 3/2005 | Cohen et al. | 600/30 |
| 7,120,499 B2 | 10/2006 | Thrope et al. | 607/48 |
| 7,328,068 B2 | 2/2008 | Spinelli et al. | 607/39 |
| 7,343,202 B2 | 3/2008 | Mrva et al. | 607/41 |
| 7,376,467 B2 | 5/2008 | Thrope et al. | 607/48 |
| 2002/0055761 A1* | 5/2002 | Mann et al. | 607/41 |
| 2004/0059392 A1* | 3/2004 | Parramon et al. | 607/36 |
| 2006/0004421 A1 | 1/2006 | Bennett et al. | 607/41 |
| 2006/0004429 A1 | 1/2006 | Mrva et al. | 607/116 |
| 2006/0287571 A1 | 12/2006 | Gozzi et al. | 600/30 |
| 2007/0123952 A1 | 5/2007 | Strother et al. | 607/48 |
| 2007/0239224 A1 | 10/2007 | Bennett et al. | 607/41 |
| 2008/0071321 A1 | 3/2008 | Boggs, II et al. | 607/39 |
| 2008/0132969 A1 | 6/2008 | Bennett et al. | 607/41 |

FOREIGN PATENT DOCUMENTS

| | | |
|---|---|---|
| WO | WO 00/19940 | 4/2000 |
| WO | WO 2007/126632 | 11/2007 |

OTHER PUBLICATIONS

U.S. Appl. No. 60/578,742, filed Jun. 10, 2004.

Caldwell, K.P.S. "Electrical Stimulation.", Sphincter Research Unit, Royal Devon and Exeter Hospital, Exeter (England), Urol. Int. 29: 225, 1974. (1 page).

Caldwell, K.P.S. "The Use of Electrical Stimulation in Urinary Retention and Incontinence [Abridged]." Section of Urology, vol. 61, pp. 35-39, Jul. 1968.

Caldwell, K.P.S. et al. "Urethral Pressure Recordings In Male Incontinents Under Electrical Stimulation." Investigative Urology vol. 5, No. 6, pp. 572-579, May 1968.

Caldwell, K.P.S. et al. "Stress Incontinence in Females: Report on 31 Cases Treated by Electrical Implant." J. Obstet. Gynaec. Brit. Cwlth vol. 75, pp. 777-780, Jul. 1968.

* cited by examiner

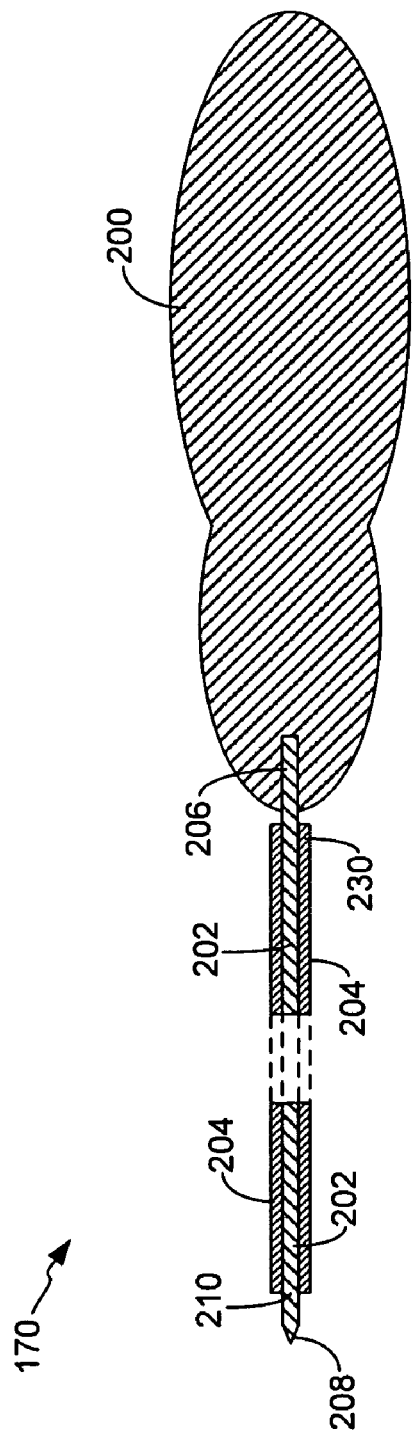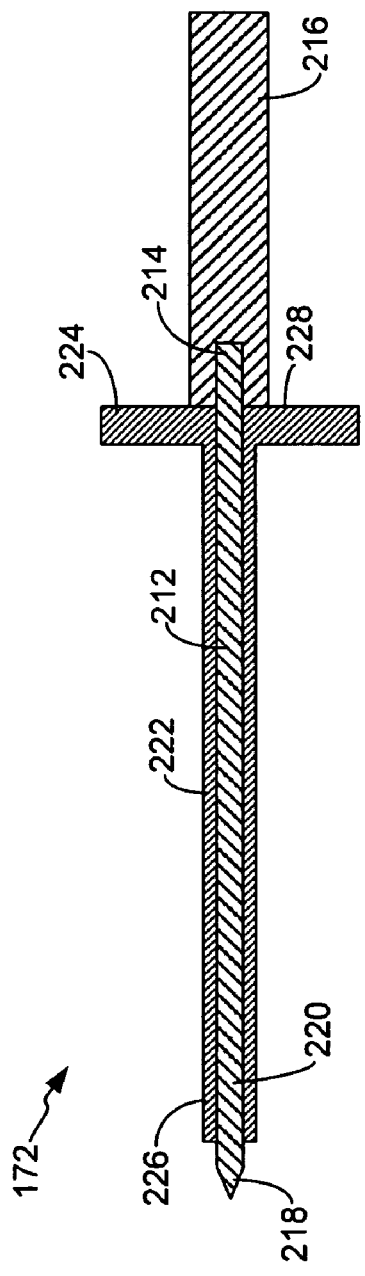

ELECTRODE IMPLANTATION IN MALE EXTERNAL URINARY SPHINCTER

CROSS-REFERENCE TO RELATED APPLICATION

The present application is based on and claims the benefit of U.S. provisional patent application Ser. No. 60/871,188, filed Dec. 21, 2006, the content of which is hereby incorporated by reference in its entirety.

FIELD OF THE INVENTION

Embodiments of the present invention generally relate to the implantation of an electrode of an electronic stimulator device into a pelvic floor muscle of a male patient and, more particularly, into an external urinary sphincter of the male patient.

BACKGROUND

Implantable electronic stimulator devices, such as neuromuscular stimulation devices, have been disclosed for use in the treatment of various pelvic conditions, such as urinary incontinence, fecal incontinence and sexual dysfunction. Such devices generally include one or more electrodes that are coupled to a control unit by leads. Electrical signals are applied to the desired pelvic muscle of the patient through electrodes in order to treat the condition. Exemplary implantable electronic stimulator devices and uses of the devices are disclosed in U.S. Pat. Nos. 6,354,991, 6,652,449, 6,712,772 and 6,862,480, each of which is hereby incorporated by reference in its entirety.

SUMMARY

Embodiments of the present invention are generally directed to a method of implanting an electrode of an electronic stimulator device into an external urinary sphincter of a male patient. In one embodiment of the method, a first incision is made in the perineum of the patient between the anus and the scrotal-perineal junction. A distal end of a stimulation lead is then fed through the first incision, through the perineal membrane and into the external urinary sphincter. The distal end includes the electrode.

In one embodiment of the method, a second incision is made in the abdomen of the patient. In one embodiment, the second incision is made lateral to and cephalad to the pubis bone of the patient. Next, a proximal end of the stimulation lead is fed from the first incision to the second incision.

In one embodiment, the proximal end of the stimulation lead is coupled to a control unit of the electronic stimulator device. Electrical signals are generated using the control unit and the electrical signals are delivered to the external urinary sphincter through the stimulation lead and the electrode.

In yet another embodiment of the method, a third incision is made in the patient that is displaced from the second incision. In one embodiment, the third incision is made in the abdomen of the patient lateral to the second incision. Next, a first end of an extension lead is coupled to the proximal end of the stimulation lead. A second end of the extension lead is fed through a subcutaneous tunnel between the second incision and the third incision and out the third incision. In one embodiment, the second end of the extension lead is coupled to a control unit of the electronic stimulator device. Electrical signals are generated using the control unit and the electrical signals are delivered to the external urinary sphincter through the extension lead, the stimulation lead and the electrode.

This Summary is provided to introduce a selection of concepts in a simplified form that are further described below in the Detailed Description. This Summary is not indented to identify key features or essential features of the claimed subject matter, nor is it intended to be used as an aid in determining the scope of the claimed subject matter. The claimed subject matter is not limited to implementations that solve any or all disadvantages noted in the Background.

BRIEF DESCRIPTION OF THE DRAWINGS

FIGS. 7 and 10 respectively are side cross-sectional views of an exemplary long introducer and an exemplary short introducer, in accordance with embodiments of the invention.

DETAILED DESCRIPTION OF ILLUSTRATIVE EMBODIMENTS

Embodiments of the present invention are directed to a method of implanting an electrode into a pelvic floor muscle of a male patient that is configured for use with an electronic stimulator device. In one embodiment of the method, an electrode is implanted in the external urinary sphincter muscle of the male patient. Before discussing various embodiments of the method of implanting the electrode, exemplary implantable electronic stimulator devices will be described with reference to FIGS. 1 and 2.

Figure 1:
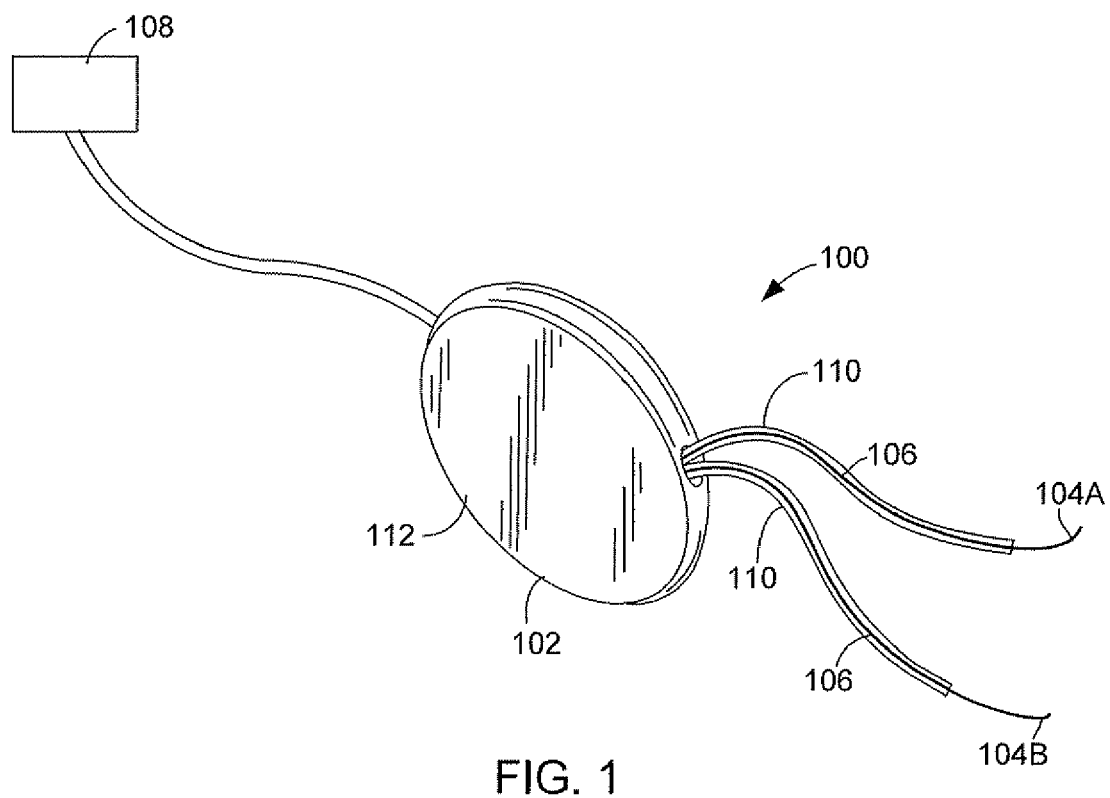
FIG. 1 is a schematic, pictorial view of an exemplary implantable electronic stimulator device in accordance with embodiments of the invention.

FIG. 1 is a schematic, pictorial view of an exemplary implantable electronic stimulator device 100, in accordance with embodiments of the invention. Device 100 is configured for implantation into the pelvic region of a patient, as described in detail below, for use in providing muscle and/or nerve stimulation that is used to control and/or treat a pelvic condition, such as pelvic pain, urinary incontinence and other pelvic conditions. In one embodiment, the device 100 comprises a control unit 102 and one or more electrodes, generally referred to as 104, such as electrodes 104A and 104B. Electrodes 104 are coupled to the control unit 102 by leads 106. In one embodiment, the device 100 includes at least one physiological sensor 108, such as a miniature ultrasound transducer, one or more accelerometers, a pressure transducer or other sensors known in the art.

In one embodiment, the control unit 102 comprises circuitry for senses electrical signals received by the electrodes 104, such as electromyogram (EMG) signals, along with circuitry for processing the signals from the sensor 108. In one embodiment, the control unit 104 comprises circuitry for applying electrical stimulation waveforms to one or more of the electrodes 104. The electrical stimulation waveforms are designed to control and/or treat the desired condition of the pelvic region.

In one embodiment, the control unit 102 and the electrodes 104 are as described in the above-referenced patents, in PCT Patent Publication WO 00-19940, entitled "Incontinence Treatment Device," and/or in PCT Patent Publication WO 00-19939, entitled "Control of Urge Incontinence," with appropriate changes as are otherwise indicated by clinical and engineering considerations that are clear to those skilled in the art.

In one embodiment, the electrodes 104 are flexible intramuscular-type wire electrodes, approximately 1-35 millimeters long and 50-100 microns in diameter, in order to minimize patient discomfort. In one embodiment, the electrodes 104 comprise a spiral hook, as known in the art, so that they can be easily and permanently anchored in a pelvic muscle of a patient. The wire, from which the electrodes 104 are made, comprises a suitable conductive material, such as a biocompatible metal such as silver, a platinum/iridium alloy (90-10) or a nickel-chromium alloy. The leads 106 have a length that is suitable for the application, such as 5-10 centimeters long, and are surrounded by an insolating jacket 110 typically comprising silicone, polyurethane or and other flexible, biocompatible insolating material. An optional additional wire (not shown) inside the jacket 110 can serve as an antenna for the purpose of wireless communications with the device 100, in accordance with known methods.

In one embodiment, the control unit 102 comprises a circuitry for processing electrical signals received from the electrodes 104 and/or for applying an electrical waveform to one or both of the electrodes 104. In one embodiment, the circuitry is contained in a case 112 made of titanium or other suitable biocompatible metal. Typically, the case 112 is about 20 millimeters in diameter and 4 millimeters thick. For some applications, the case 112 serves as a ground electrode for the electrodes 104 when they are sensing or stimulating in a monopolar mode. Alternatively, the case 112 may comprise metal coated with a layer of biocompatible plastic, such as polymethyl methacrylate (PMMA) or silicon.

Figure 2:
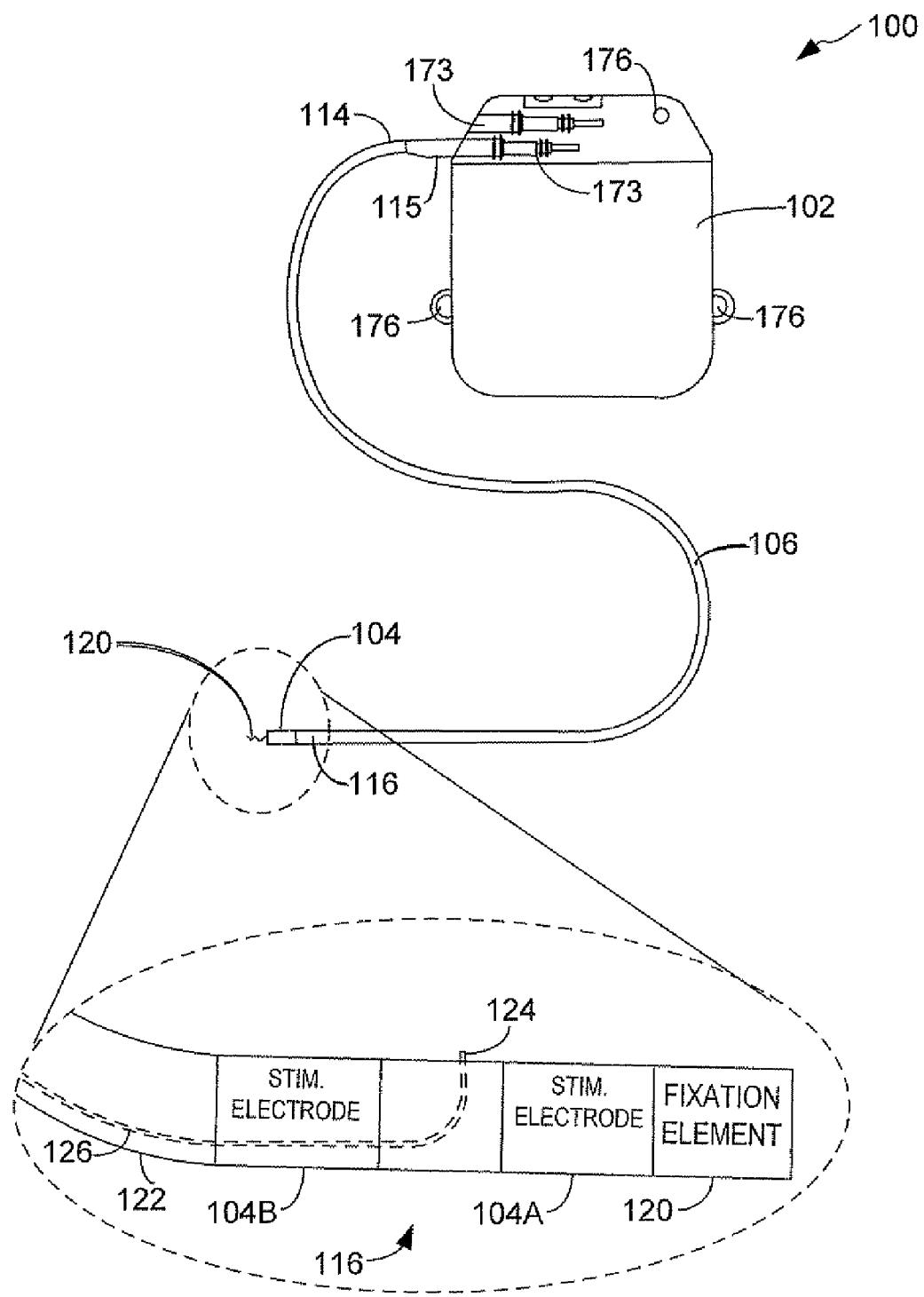
FIG. 2 is a side plan view of an exemplary electronic stimulator device, in accordance with embodiments of the invention.

Although two electrodes 104A and 104B and one sensor 108 are shown attached to the control unit 102 in FIG. 1, it is possible to use only a signal electrode 104 as illustrated in FIG. 2, which is a side plan view of an exemplary electronic stimulator device 100, in accordance with another embodiment of the invention. Except with respect to the difference described below, the embodiment of the device 100 shown in FIG. 2 is generally similar to the embodiments shown in FIG. 1, and techniques described herein with respect to one of these configurations can generally be applied to the other configuration. Accordingly, elements in FIG. 2 that are labeled with the same or similar numbers as that used in FIG. 1, generally correspond to the same or similar elements.

One embodiment of the device 100 shown in FIG. 2 comprises a control unit 102, at least one electrode 104 and a lead 106 connecting electrode 104 to the control unit 102. The lead 106 includes a proximal end 114 that is coupled to the control unit 102 via a connector 115 and a distal end 116 at which the electrode 104 is located. Additional leads 106 or sensors 108 may be coupled to the control unit 102 at a suitable interface, such as interface 118.

The electrode 104 can be anchored to a pelvic floor muscle of the patient by means of a fixation element 120, such as a helix, spiral hook or other anchor known in the art, as shown in the magnified schematic illustration of the distal end 116 of the lead 106 provided in FIG. 2. The helix or spiral hook 120 can be embedded within the external urinary sphincter to anchor the lead 106 thereto. In one embodiment, the fixation element 120 operates to provide electrical contact between the muscle and one or more stimulation electrodes 104A and 104B disposed on a silicone casing 122 of the lead 106.

In one embodiment, the electrodes, generally referred to as 104, are approximately 3 millimeters in length, but can be much longer, such as less than about 80 millimeters in length, for example. The electrodes 104 are typically separated by approximately 3 millimeters along the length of the lead 106. In the same between the electrodes 104A and 104B a tip 124 of an EMG wire 126 may protrude approximately 100 microns through the casing 124, for those applications in which EMG sensing is desirable. Typically, the diameter of the wire 126 is approximately 50 microns, and the diameter of the casing 124 is approximately 1.5 millimeters.

As with the device 100 illustrated in FIG. 1, one embodiment of the device 100 illustrated in FIG. 2 comprises circuitry for applying electrical stimulation waveforms to the muscular tissue, in which the fixation element 120 is embedded and/or for sensing electrical signals received by the electrodes 104, in accordance with conventional implantable electronic stimulator devices known in the art.

Figure 3:
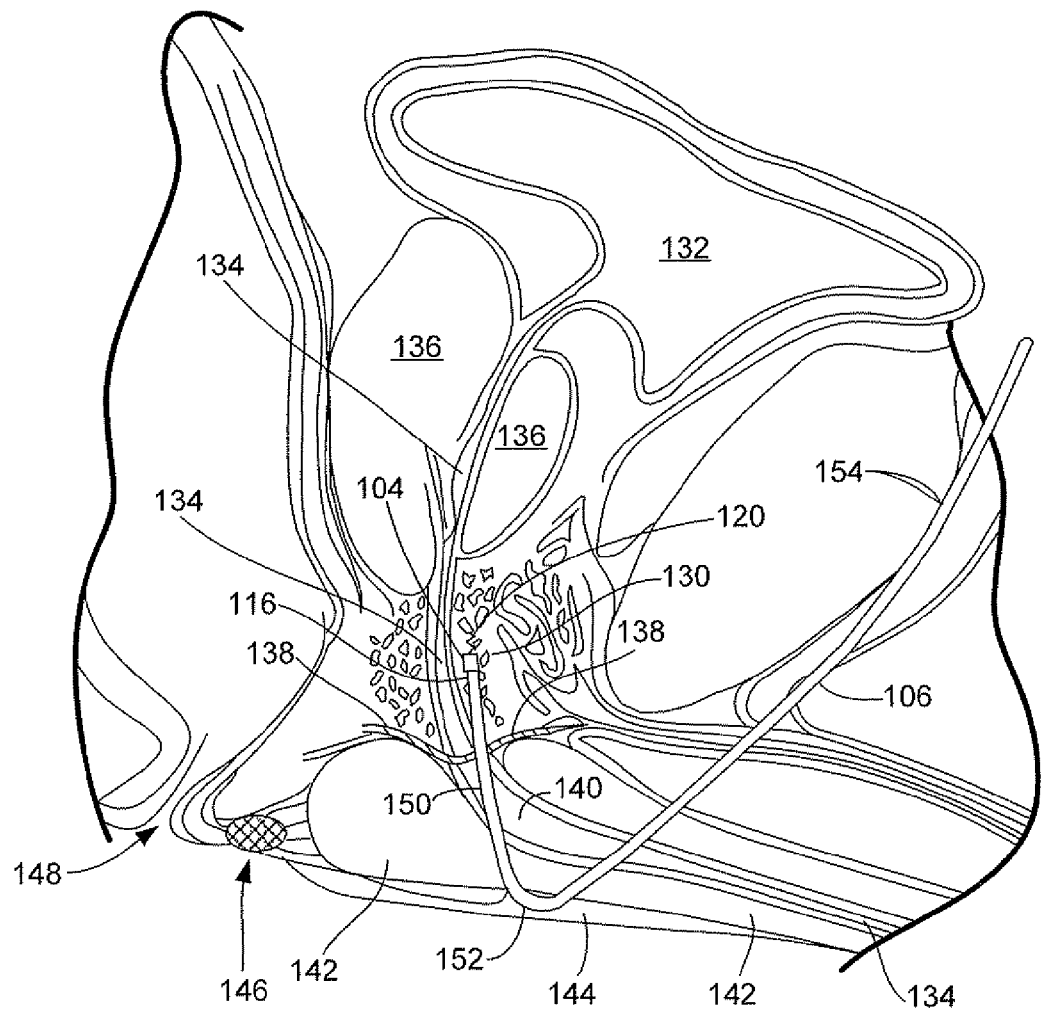
FIGS. 3 and 4 illustrate the general pelvic anatomy of a male patient and a location of a stimulation lead in accordance with embodiments of the invention.
Figure 4:
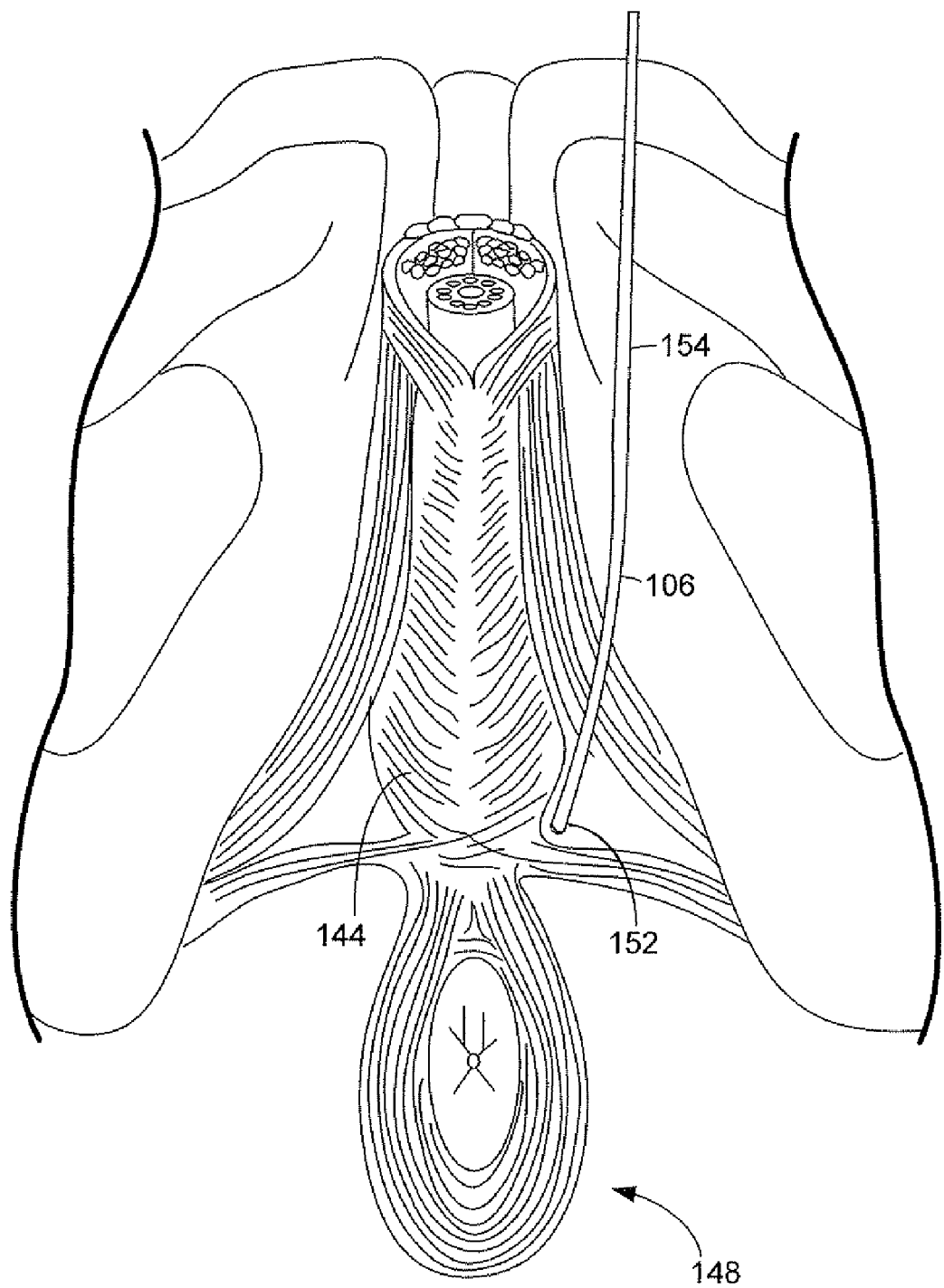

Embodiments of the invention are directed to a method of installing the distal end 116 of the stimulation lead 106 in the lateral aspect of the external urinary sphincter muscle 130 of a male patient, as shown in FIG. 3, which is a partly sectional illustration of a pelvic region of a male patient. In one embodiment, the one or more electrodes 104 at the distal end 116 of the lead 106 is anchored to the external urinary sphincter muscle 130 of the male patient using the fixation element 120, in accordance with known methods. Alternatively, the electrode 104 may be installed in a location of the pelvic floor region that is adjacent to the urinary sphincter muscle 130 of the male patient through which the stimulation signals generated by the control unit 102 can provide the desired treatment of the targeted pelvic condition.

Certain pelvic anatomy is illustrated in FIG. 3 including the bladder 132 that connects to a proximal end of the urethra 134, at the bladder neck. The urethra 134 extends distally from the bladder 132 through the prostate 136 and below the prostate 136 through the perineal membrane 138 (the portion of the urethra associated with the perineal membrane 138 can be referred to as the "membranous urethra"). Portion 140 of the urethra 134 located distally relative to the perineal membrane 138 is referred to as the "bulbar urethra" 140. Tissue below the perineal membrane 138 and the bulbar urethra 140 includes the corpus spongiosum 142 and the bulbospongiosus muscle 144. The central tendon 146 connects the posterior of the corpus spongiosum 142 and the bulbospongiosus muscle 144, adjacent to the anus 148.

In accordance with one embodiment, a distal portion 150 of the lead 106 extends vertically approximately parallel to the rectum 148 and the urethra 134 toward the apex of the prostate 136. The distal end 116 of the lead 106 pierces the perineal membrane 138 and is anchored in the external urinary sphincter 130 by the fixation element 120. As a result, one or more electrodes 104 at the distal end 116 of the lead 106 are located such that they can either sense signals conducted through the external urinary sphincter 130 or apply electrical signals to the external urinary sphincter 130. A portion 152 of the lead 106 is bent proximate the perineum such that a proximal portion 154 extends past the spermatic cord, however, the proximal portion 154 of the lead 106 can also be placed over the spermatic cord if desired.

Figure 5:
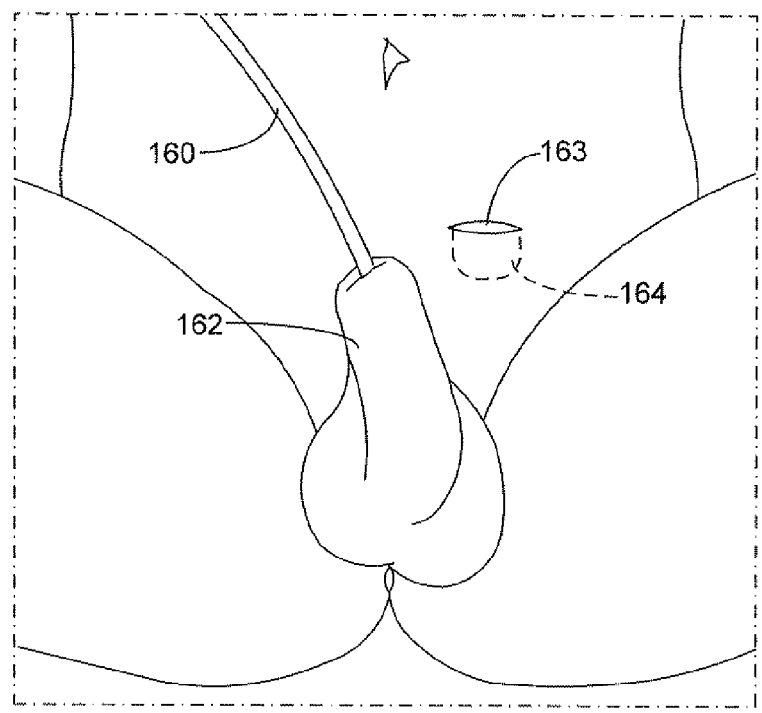
FIGS. 5, 6, 8, 9 and 11-16 illustrate various steps of a method of implanting an electrode of an electronic stimulator device in an external urinary sphincter of a male patient, in accordance with embodiments of the invention.

Embodiments of the invention are directed to a method of implanting at least one electrode 104 in contact with the external urinary sphincter 130 of a male patient, as described above. Initially, after the patient has been properly prepared for surgery, the male patient is positioned in a dorsal lithotomy position, in which the hips are flexed, the legs are elevated in stirrups, and the buttocks are even with an edge of the table, as illustrated in FIG. 5. In one embodiment of the method, a catheter 160 (e.g., 14 F Foley catheter) is inserted into the urethra of the penis 162. The bladder of the patient is preferably checked to determine that it is empty using the catheter 160. The catheter 160 can also be used to identify the urethra of the patient during subsequent steps of the method.

An incision 163 is formed in the subcutaneous tissue adjacent to the fascia using blunt dissection to form an abdominal pocket 164, as shown in FIG. 5. In one embodiment, the incision 163 comprises a 2-3 centimeter long, horizontal skin incision that is approximately 6 centimeters lateral to and 4 centimeters cephalad to the pubis bone of the patient. In one embodiment, the abdominal pocket 164 is sized to accommodate a control unit of an implantable electronic stimulator device, such as one of the exemplary control units 102 described above. Thus, for example, the abdominal pocket 164 may comprise a depth of approximately 4 centimeters in order to accommodate the control unit 102. An antibiotic soaked pad may be placed in the abdominal pocket 164.

Figure 6:
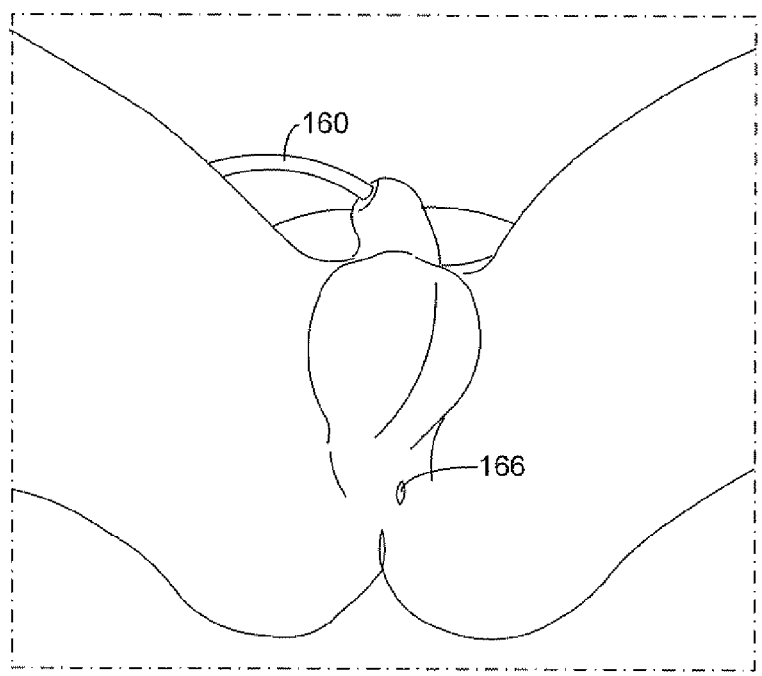

With reference to FIG. 6, a small incision 166 is made in the perineum down to the subcutaneous tissue (i.e., the fascia should be visible). In one embodiment, the incision 166 is a vertical incision that is approximately 1-1.5 centimeters long and is approximately 1.5 centimeters lateral to the midline of the perineum, halfway between the anus 148 and the scrotal-perineal junction. In one embodiment, the incision 166 is made on the same side as the abdominal pocket 164 (FIG. 5).

Figure 8:
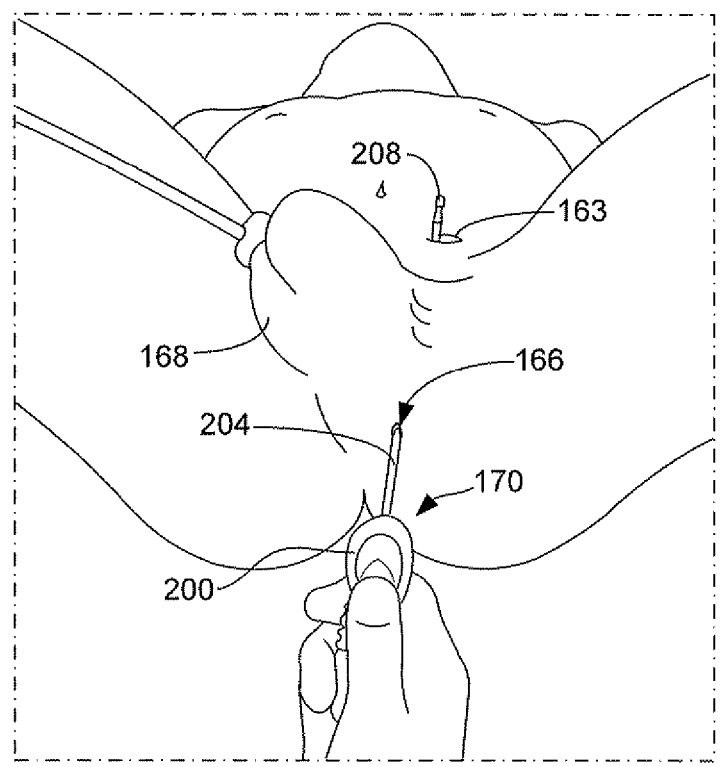

With the scrotum 168 held firmly aside, a long introducer 170 is fed through the anterior aspect of the perineal incision 166. FIG. 7 is a side cross-sectional view of an exemplary long introducer 170 in accordance with embodiments of the invention. The introducer 170 is formed of biocompatible materials and generally comprises a handle 200, a stainless steel needle guide 202, and a removable sheath or tube 204. The needle guide 202 comprises a proximal end 206 that is coupled to the handle 200 and a needle tip 208 located at a distal end 210. The needle tip 208 of the introducer 170 is carefully fed past the spermatic cord (preferably under the spermatic cord) and the needle tip 208 is worked up toward and then through the suprapubic incision 163 that forms the abdominal pocket 164 to create a subcutaneous tunnel between the incision 163 and the incision 166. The subcutaneous tunnel is preferably made as superficial as possible from the perineal incision 166 to the abdominal pocket 164. The guide needle 202 of the introducer 170 is removed leaving the long introducer sheath 204 extending through the perineal incision 166 through the subcutaneous tunnel and out the incision 163, as shown in FIG. 8.

Figure 9:
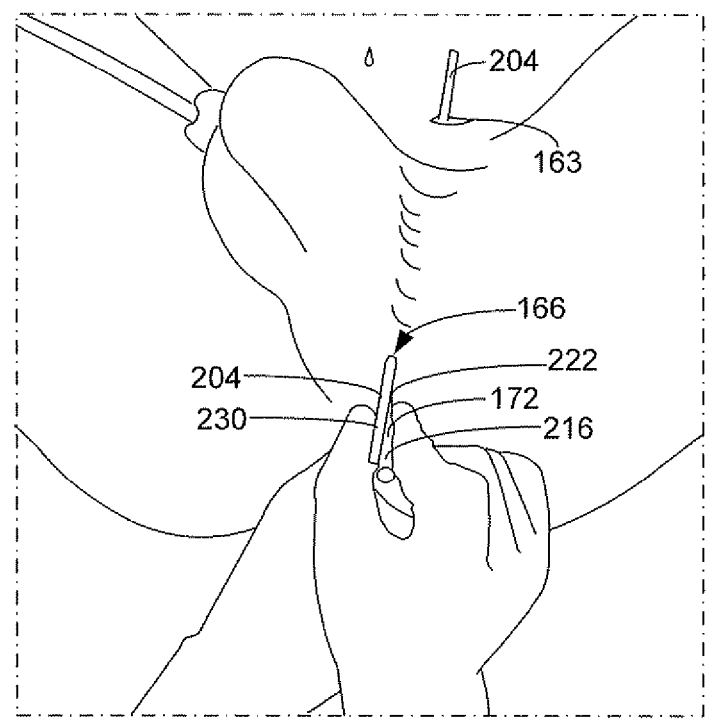

In one embodiment of the method, the short introducer 172 is carefully inserted into the perineal incision 166, as shown in FIG. 9. FIG. 10 is a side cross-sectional view of an exemplary short introducer 172 in accordance with embodiments of the invention. The short introducer 172 is formed of biocompatible materials and generally comprises a guide needle 212 having a proximal end 214 coupled to a handle 216 and a needle tip 218 at a distal end 220. The guide needle 212 is extended through a tube or sheath 222. The operator may remove the needle 212 from the sheath 222 by pulling on the handle 216 while holding the sheath 222 in place by pressing on a flange 224 of the sheath 222.

The needle tip 218 is advanced approximately parallel to the rectum 148 and urethra 134 (FIG. 3) and towards the apex of the prostate 136 (FIG. 3) (or catheter balloon in the event that the catheter 160 is present), as illustrated in FIG. 9. It is important to ensure that the needle tip 218 of the short introducer 172 is advanced along a path that does not intersect the rectum 138 or the urethra 134. In one embodiment of the method, a transrectal ultrasound probe is inserted in the rectum 148 of the patient and used by the surgeon to visualize the path of the needle tip 218 and ensure that the needle tip 218 enters the lateral aspect of the external urinary sphincter 130 of the patient.

The needle tip 218 of the short introducer 172 is advanced along the desired path until the needle tip 218 encounters the tissue of the external urinary sphincter 130. In general, the detection of an increase in resistance to the further advancement of the short introducer 172 followed by a small "pop" as the needle tip 218 pierces the perineal membrane 138 (FIG. 3) will indicate that the needle tip 218 has entered the external urinary sphincter 130. In one embodiment, the needle tip 218 is advanced approximately 0.5-1 additional centimeters to ensure that it is located sufficiently deep within the tissue of the external urinary sphincter 130. In one embodiment, the transrectal ultrasound probe is used to verify that the needle tip 218 of the short introducer 172 is properly positioned in the manner illustrated in FIG. 3, with respect to the patient's anatomy. Next, the introducer or guide needle 212 of the short introducer 172 is carefully removed without disturbing the position of the introducer sheath 222.

Figure 11:
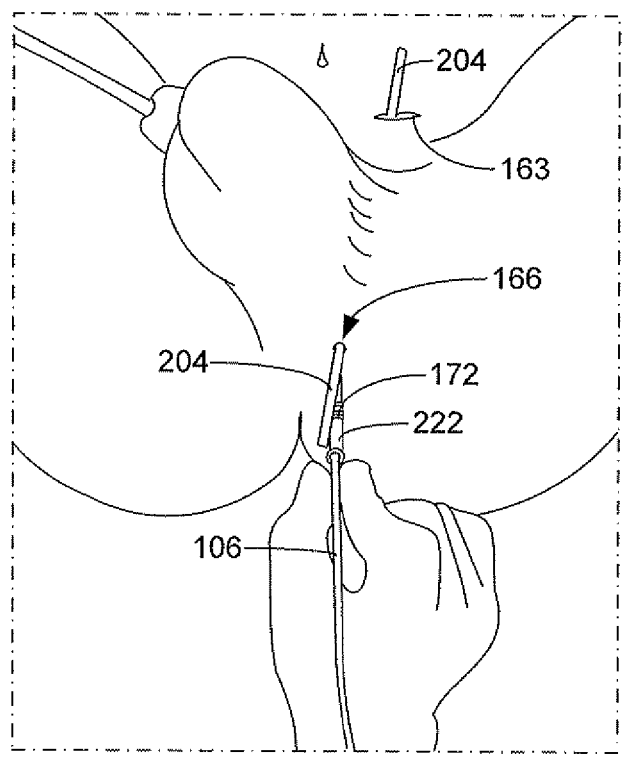

Next, the distal end 116 of the lead 106 is inserted into the short introducer sheath 222 until the fixation element 120 extends through the distal end 226 of the introducer sheath 222, as illustrated in FIG. 11. In one embodiment, the lead 106 includes a marking that indicates when this occurs. For example, when the markings on the lead 106 align with the proximal end 228 of the introducer sheath 222, it is known that the distal end 116 or the fixation element 120 of the lead 106 extends through the distal end 226 of the introducer sheath 222 and into the external urinary sphincter 130.

In one embodiment, while holding the lead 106 near the introducer sheath 222, the lead 106 is twisted a few rotations to place the fixation element 120 (e.g., spiral hook) of the lead 106 into the tissue of the external urinary sphincter 130. In one embodiment, a stiffening wire is introduced into the introducer sheath 222 along with the lead 106 to aid in the rotation of the lead 106.

Once the distal end 116 of the lead 106 is anchored into the tissue of the external urinary sphincter 130, the introducer sheath 222 is removed from the wound channel. In one embodiment, the introducer sheath 222 is split in half along a weakened longitudinal breaking line of the sheath 222 to remove it from the lead 106.

In accordance with one embodiment, a suture, such as a 4.0 Vicryl suture, is placed in the subcutaneous tissue, in the posterior aspect of the perineal incision 166. The lead 106 is then secured with the suture by wrapping the suture around the portion 152 of the lead 106.

Figure 12:
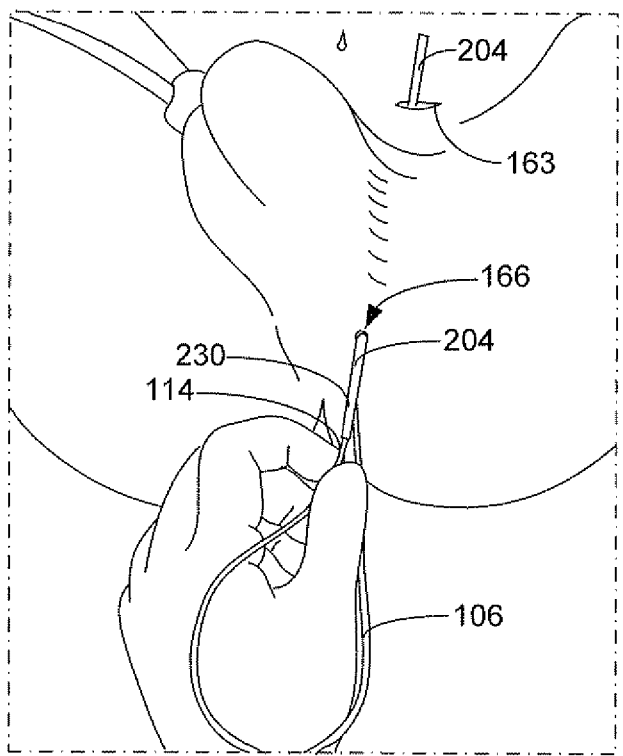
Figure 13:
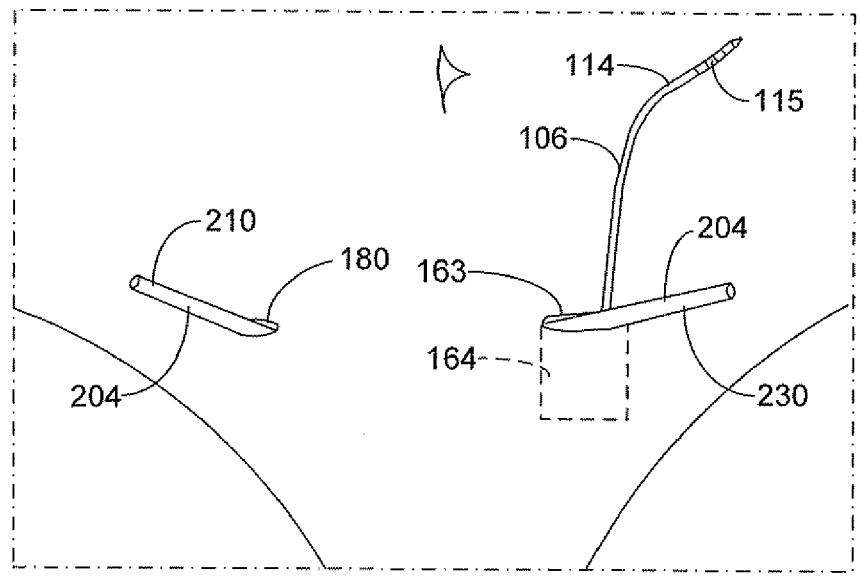

Next, the proximal end 114 (FIG. 2) of the lead 106 is inserted into the proximal end 230 of the long introducer tube 204, as shown in FIG. 12. The connector portion 115 of the lead 106 should be fully inserted into the proximal end 230 of the long introducer tube 204 and secured within the tube 204 by frictional resistance or other suitable means. The long introducer tube 204 is then pulled up toward the suprapubic incision 163 carefully as to not lose the connection to the lead 106. The long introducer tube 204 is then pulled completely through the suprapubic incision 163 while leaving the portion 154 of the lead 106 within the subcutaneous tunnel formed by the long introducer tube 204, as shown in FIG. 3. The proximal end 114 of the lead 106 is then removed from the proximal end 230 of the long introducer tube 204 and left outside of the abdominal pocket 164, as shown in FIG. 13. In one embodiment, a second suture, such as 4.0 Vicryl suture, is placed in the anterior aspect of the perineal incision 166 and is used to fixate the portion 152 (FIG. 3) of the lead 106. In one embodiment, the anterior suture is loosely tied to the portion 152 of the lead 106. Slack in the lead 106 is eliminated by pulling the lead 106 through the abdominal pocket 164. Once the slack in the lead 106 has been eliminated, the lead 106 can be firmly affixed using the anterior suture.

In accordance with one embodiment, the connecting portion 115 of the lead 106 is installed in a corresponding socket 173 of the control unit 102, as shown in FIG. 2, to complete the assembly of the electrical stimulation device 100. In one embodiment, a seal is formed between the socket 173 and the connector 115 using an o-ring or other suitable component, to prevent fluids from entering the socket 173. Set screws are used to secure the connector 115 within the socket 173.

Figure 14:
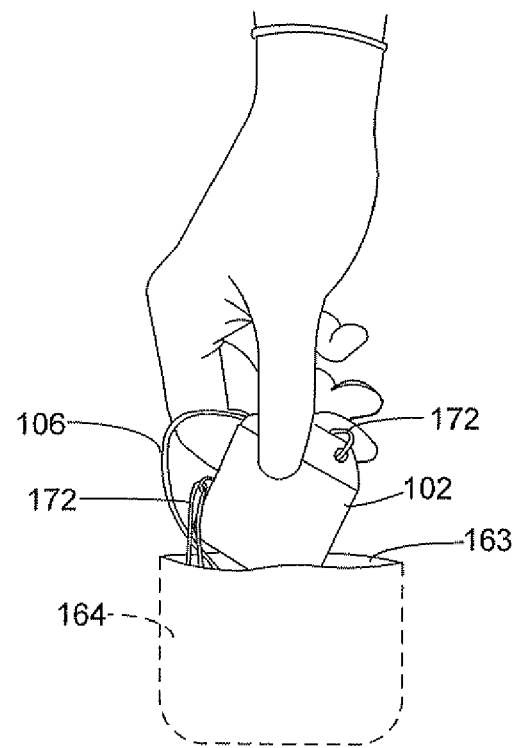

The device 100 is preferably tested to ensure that it is working properly including generating the desired electrical waveforms and applying the electrical waveforms or signals to the external urinary sphincter 130 through the electrode 104 and/or performing another desired functions. If the device 100 is operating properly, the lead 106 is tucked into the abdominal pocket 164 and sutures 174 are looped through suture holes 176 (FIG. 2) and used to secure the control unit 102 to the fascia within the pocket, as illustrated in FIG. 14. In one embodiment, the control unit 102 is located 4 centimeters or less from the surface of the skin in the subcutaneous tissue to allow the unit 102 to receive programming signals. Once the control unit 102 is secured within the abdominal pocket 164, the incision 163 is sealed to complete the implantation of the device 100 in the patient.

It may be desirable to test the device 100 for one to three weeks to determine whether the device 100 is working properly and/or whether the patient is a suitable candidate for the device 100. In accordance with one embodiment of the method, the control unit 102 is not connected to the connector 115 of the lead 106 following the feeding of the proximal end 114 through the subcutaneous incision 163, and the control unit is not installed in the abdominal pocket 164. Rather, an incision 180, such as a horizontal incision approximately 1 centimeter long, is made on the contralateral side of the patient's abdomen, as shown in FIG. 13. In one embodiment, the incision 180 is approximately 15 centimeters from the initial abdomen incision 163.

Figure 15:
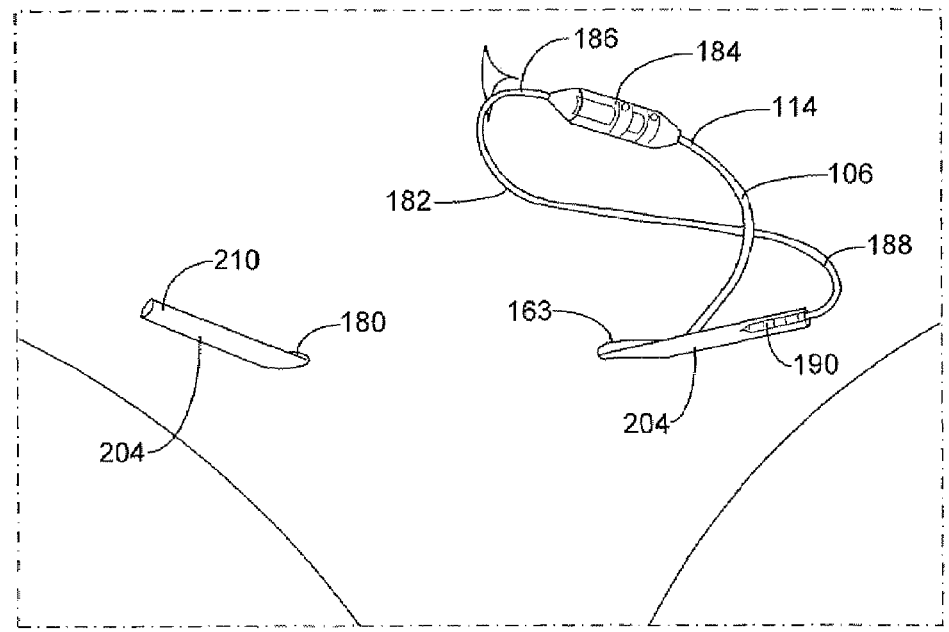

The long introducer 170 with its tube 204 is used to form a subcutaneous tunnel from the initial abdomen incision 163 to the incision 180 and the introducer needle 202 is removed to leave the tube 204 in place with the proximal end 230 extending through the incision 163 and the distal end 210 extending through the incision 180, as shown in FIG. 13. An extension lead 182 is provided that includes a socket 184 at a first end 186, to which the connector 115 of the lead 106 is attached, as illustrated in FIG. 15. In one embodiment, the socket 184 receives the connector 115 and set screws are used to secure the connection. A seal is formed between the socket 184 and the connector 115 using an o-ring or other suitable component to prevent fluids from entering the socket 184. A second end 188 of the extension lead 182 includes a connector 190 that is configured to be received by the control unit 102.

Figure 16:
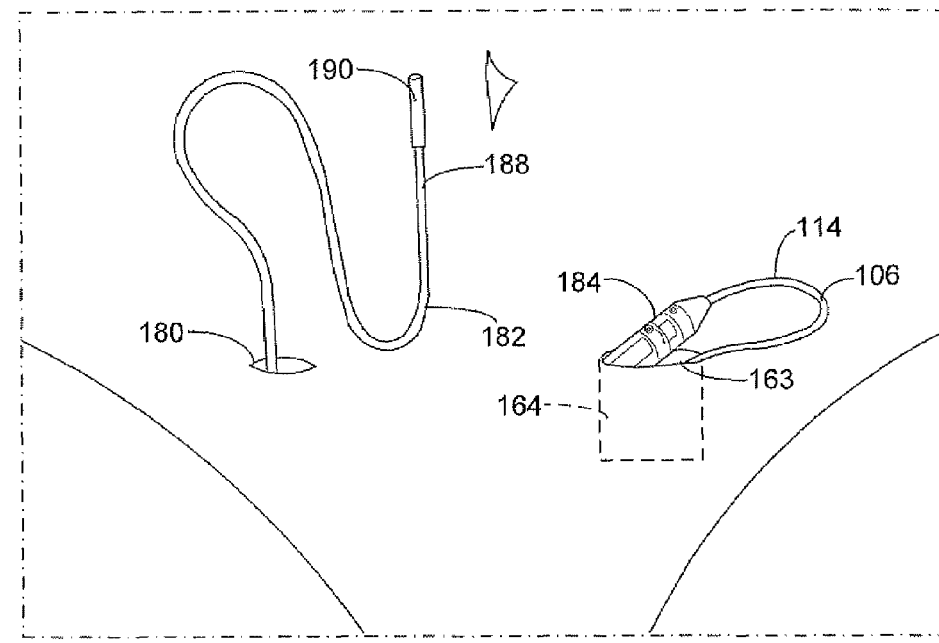

The connector 190 is then secured in the proximal end 230 of the tube 204 by frictional resistance or other suitable means, as illustrated in FIG. 15. The tube 104 is then carefully pulled completely through the incision 180 along with the second end 188 of the extension lead 182 and the connector 190 is removed from the proximal end 230 of the tube leaving the end 188 of the extension lead 182 extending out of the incision 180, as illustrated in FIG. 16. Slack is removed from the extension lead 182.

The socket 184 of the extension lead 182 and the proximal end 114 of the lead 106 are packed into the abdominal pocket 164, as illustrated in FIG. 16. The incision 163 is then closed over the lead extension socket 184 in two layers.

The connector 190 is then installed in the socket 173 of the control unit and secured with set screws. The connection of the control unit 102 to the extension lead 182 via connector 190, and the extension lead 182 to the lead 106 via the installation of the connector 115 in the socket 184, allows the control unit 102 to send electrical signals to, and/or receive electrical signals from, the electrode 104. The control unit can be worn on a belt outside of the body of the patient. Thus, testing of the device 100 with the implanted electrode 104 in the external urinary sphincter 130 of the patient can commence.

If the testing of the device 100 and the installed lead 106 is successful, the incision 163 can be reopened to expose the socket 184 and the connector 115. The connector 115 is disconnected from the socket 184 and the extension lead 182 is pulled through the incision 180. The connector 115 can then be installed directly in the socket 173 of the control unit and installed in the abdominal pocket as described above to complete the implantation of the device 100 in the patient.

Although the present invention has been described with reference to preferred embodiments, workers skilled in the art will recognize that changes may be made in form and detail without departing from the spirit and scope of the invention.

What is claimed is:

1. A method of implanting an electrode of an electronic stimulator device into an external urinary sphincter of a male patient, the method comprising:

making a first incision in the perineum between the anus and the scrotal-perineal junction; and feeding a distal end of a stimulation lead through the first incision, through the perineal membrane and into the external urinary sphincter, the distal end comprising the electrode.

2. The method of claim 1, wherein feeding a distal end of a stimulation lead through the first incision, through the perineal membrane and into the external urinary sphincter comprises:

installing a first tube having a first end proximate the first incision and a second end that extends through the perineal membrane and into the external urinary sphincter; and feeding the distal end of the stimulation lead through the first tube, out the second end of the first tube and in contact with the external urinary sphincter.

3. The method of claim 2, wherein installing a first tube having a first end proximate the first incision and a second end that extends through the perineal membrane and into the external urinary sphincter comprises:

providing a first introducer comprising a needle guide within the first tube;

tunneling from the first incision through the perineum and into the external urinary sphincter using the needle guide; and removing the needle guide from the first tube.

4. The method of claim 3, further comprising:

making a second incision in the abdomen of the patient;

installing a second tube having a first end proximate the first incision and a second end proximate the second incision;

attaching a proximal end of the stimulation lead to the first end of the second tube; and pulling the second tube and the proximal end of the stimulation lead out of the second incision.

5. The method of claim 4, further comprising:
coupling the proximal end of the stimulation lead to a control unit of the electronic stimulator device;
generating electrical signals using the control unit; and
delivering the electrical signals to the external urinary sphincter through the stimulation lead and the electrode.

6. The method of claim 5, further comprising:
forming a subcutaneous pocket at the second incision; and
implanting the control unit in the subcutaneous pocket.

7. The method of claim 5, wherein the electrical signals are configured to treat a pelvic condition selected from the group consisting of pelvic pain and urinary incontinence.

8. The method of claim 4, further comprising:
making a third incision that is displaced from the second incision;
coupling a first end of an extension lead to the proximal end of the stimulation lead; and
feeding a second end of the extension lead through a subcutaneous tunnel between the second incision and the third incision and out the third incision.

9. The method of claim 8, wherein feeding a second end of the extension lead through a subcutaneous tunnel between the second incision and the third incision and out the third incision comprises:
installing a third tube in the subcutaneous tunnel having a first end proximate the third incision and a second end proximate the second incision;
attaching a second end of the extension lead to the second end of the third tube; and
pulling the third tube and the second end of the extension lead through the subcutaneous tunnel and out of the third incision.

10. The method of claim 8, further comprising:
coupling the second end of the extension lead to a control unit of the electronic stimulator device;
generating electrical signals using the control unit; and
delivering the electrical signals to the external urinary sphincter through the extension lead, the stimulation lead and the electrode.

11. The method of claim 10, further comprising:
disconnecting the second end of the extension lead from the control unit;
disconnecting the first end of the extension lead from the proximal end of the stimulation lead;
removing the extension lead from the subcutaneous tunnel;
coupling the proximal end of the stimulation lead to the control unit;
generating electrical signals using the control unit; and
delivering the electrical signals to the external urinary sphincter through the stimulation lead and the electrode.

12. The method of claim 11, further comprising:
forming a subcutaneous pocket at the second incision; and
implanting the control unit in the subcutaneous pocket.

13. The method of claim 11, wherein the electrical signals are configured to treat a pelvic condition selected from the group consisting of pelvic pain and urinary incontinence.

14. The method of claim 8, wherein the second incision is located lateral to and cephalad to the pubis bone of the patient.

15. The method of claim 2, further comprising:
anchoring the distal end of the stimulation lead to the external urinary sphincter; and removing the first tube while the distal end of the stimulation lead remains anchored to the external urinary sphincter.

16. A method of implanting an electrode of an electronic stimulator device into an external urinary sphincter of a male patient, the method comprising:
making a first incision in the perineum between the anus and the scrotal-perineal junction;
feeding a distal end of a stimulation lead through the first incision, through the perineal membrane and into the external urinary sphincter, the distal end comprising the electrode;
making a second incision in the abdomen of the patient; and
feeding a proximal end of the stimulation lead from the first incision to the second incision.

17. The method of claim 16, wherein feeding a distal end of a stimulation lead through the first incision, through the perineal membrane and into the external urinary sphincter comprises:
installing a first tube having a first end proximate the first incision and a second end that extends through the perineal membrane and into the external urinary sphincter; and
feeding the distal end of the stimulation lead through the first tube, out the second end of the first tube and in contact with the external urinary sphincter.

18. The method of claim 17, wherein installing a first tube having a first end proximate the first incision and a second end that extends through the perineal membrane and into the external urinary sphincter comprises:
providing a first introducer comprising a needle guide within the first tube;
tunneling from the first incision through the perineum and into the external urinary sphincter using the needle guide; and
removing the needle guide from the first tube.

19. The method of claim 17, wherein feeding a proximal end of the stimulation lead from the first incision to the second incision comprises:
installing a second tube having a first end proximate the first incision and a second end proximate the second incision;
attaching a proximal end of the stimulation lead to the first end of the second tube; and
pulling the second tube and the proximal end of the stimulation lead out of the second incision.

20. The method of claim 16, further comprising:
coupling a proximal end of the stimulation lead to a control unit of the electronic stimulator device;
generating electrical signals using the control unit; and
delivering the electrical signals to the external urinary sphincter through the stimulation lead and the electrode.

21. The method of claim 20, further comprising:
forming a subcutaneous pocket at the second incision; and
implanting the control unit in the subcutaneous pocket.

22. The method of claim 20, wherein the electrical signals are configured to treat a pelvic condition selected from the group consisting of pelvic pain and urinary incontinence.

23. The method of claim 16, further comprising:
making a third incision that is displaced from the second incision;
coupling a first end of an extension lead to the proximal end of the stimulation lead; and
feeding a second end of the extension lead through a subcutaneous tunnel between the second incision and the third incision and out the third incision.

24. The method of claim 21, further comprising:
coupling the second end of the extension lead to a control unit of the electronic stimulator device;
generating electrical signals using the control unit; and
delivering the electrical signals to the external urinary sphincter through the extension lead, the stimulation lead and the electrode.

25. The method of claim 24, further comprising:
disconnecting the second end of the extension lead from the control unit;
disconnecting the first end of the extension lead from the proximal end of the stimulation lead;
removing the extension lead from the subcutaneous tunnel;
coupling the proximal end of the stimulation lead to the control unit;
generating electrical signals using the control unit; and
delivering the electrical signals to the external urinary sphincter through the stimulation lead and the electrode.

* * * * *

UNITED STATES PATENT AND TRADEMARK OFFICE
CERTIFICATE OF CORRECTION

PATENT NO. : 7,647,113 B2
APPLICATION NO. : 11/961615
DATED : January 12, 2010
INVENTOR(S) : Alan G. Wirbisky et al.

It is certified that error appears in the above-identified patent and that said Letters Patent is hereby corrected as shown below:

Column 11
Line 1, replace "21" with --23--.

Signed and Sealed this

Sixteenth Day of March, 2010

David J. Kappos
*Director of the United States Patent and Trademark Office*